US00PP22484P2

(12) United States Plant Patent
Stemkens

(10) Patent No.: US PP22,484 P2
(45) Date of Patent: Feb. 7, 2012

(54) *VERBENA* PLANT NAMED 'PLUFRENA'

(50) Latin Name: *Verbena×hybrida*
Varietal Denomination: Plufrena

(75) Inventor: Henricus Godefriedus Wilhelmus Stemkens, Ehkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/924,085

(22) Filed: Sep. 20, 2010

(51) Int. Cl.
*A01H 5/00* (2006.01)

(52) U.S. Cl. ..... Plt./308

(58) Field of Classification Search ..... Plt./308
See application file for complete search history.

*Primary Examiner* — Susan McCormick Ewoldt
(74) *Attorney, Agent, or Firm* — S. Matthew Edwards

(57) ABSTRACT

A new *Verbena* plant named 'Plufrena' particularly distinguished by the bold red-purple colored flowers with lighter centers, medium green foliage, medium sized creeping and trailing plant habit with good branching and is early to flower.

1 Drawing Sheet

Latin name of the genus and species of the plant claimed: *Verbena×hybrida.*

Varietal denomination: 'Plufrena'.

BACKGROUND OF THE NEW PLANT

The present invention comprises a new *Verbena*, botanically known as *Verbena×hybrida*, and hereinafter referred to by the variety name 'Plufrena'.

'Plufrena' is a product of a planned breeding program. The new cultivar has bold red-purple colored flowers with lighter centers, medium green foliage, medium sized creeping and trailing plant habit with good branching and is early to flower.

'Plufrena' originated from a open pollinated hybridization made in summer of 2004 in a controlled breeding environment in Enkhuizen, Netherlands. The female parent was the unpatented, proprietary plant designated 'E0723-6' with purple flowers, fewer flowers and has less seed set.

The male parent of 'Plufrena' was an unpatented proprietary plant designated as 'G1368-1' with smaller deep rose flowers, with foliage with fewer incisions. The resultant seed was sown in February 2005.

'Plufrena' was selected as one flowering plant within the progeny of the stated cross in the August 2005 in a controlled environment in Enkhuizen, Netherlands.

The first act of asexual reproduction of 'Plufrena' was accomplished when vegetative cuttings were propagated from the initial selection in August 2005 in a controlled environment in Enkhuizen, Netherlands.

BRIEF SUMMARY OF INVENTION

Horticultural examination of plants grown from cuttings of the plant initiated in August 2005, and continuing thereafter, has demonstrated that the combination of characteristics as herein disclosed for 'Plufrena' are firmly fixed and are retained through successive generations of asexual reproduction.

'Plufrena' has not been observed under all possible environmental conditions. The phenotype may vary significantly with variations in environment such as temperature, light intensity and day length.

Plant Breeder's Right for this cultivar were applied for in Canada on Feb. 9, 2010 (10-6832) and in CPVO on Sep. 29, 2009 (2009/1914). 'Plufrena' has not been made publicly available more than one year prior to the filing of this application.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawing shows typical flower and foliage characteristics of 'Plufrena' with colors being as true as possible with an illustration of this type. The photographic drawing shows a flowering potted plant of the new variety, and a close-up of the flowers.

DETAILED BOTANICAL DESCRIPTION

The aforementioned photographs were taken in April 2010 from plants growing in a greenhouse trial in Gilroy, Calif. USA. These plants were growing in 4 inch pots and were approximately 15-16 weeks of age.

The plant descriptions and measurements were taken in late May 2010 in Enkhuizen, Netherlands on about 12 week old plants that had been planted into 12 cm pots and were grown on benches in a greenhouse at a minimum temperature (heating temperature) of 12° C. From April on, a minimum night temperature of 8° C. was held, while day temperatures were much higher, depending on outdoor temperature.

Color references are made to The Royal Horticultural Society Colour Chart (R.H.S.) 2001.

TABLE 1

DIFFERENCES BETWEEN THE NEW VARIETY 'PLUFRENA' AND A SIMILAR VARIETY

| | 'Plufrena' | 'Balazmapurp' (U.S. Plant Pat. No. 16,525) |
|---|---|---|
| Flower color: | Red-purple | Purple-violet |
| Peduncle length: | Longer | Shorter |

TABLE 1-continued

DIFFERENCES BETWEEN THE NEW VARIETY 'PLUFRENA' AND A SIMILAR VARIETY

| | 'Plufrena' | 'Balazmapurp' (U.S. Plant Pat. No. 16,525) |
|---|---|---|
| Stigma color: | RHS 143B | RHS 145A |
| Pistil length: | Longer | Shorter |

Plant:

*Form, growth and habit.*—Herbaceous, initially spreading, later becoming decumbent to trailing.

*Plant height.*—About 7 cm.

*Plant height (inflorescence included).*—10-12 cm.

*Plant width.*—About 37 cm.

Roots:

*Number of days to initiate and produce roots.*—About 10-14 days at about 22 degrees C.

*Type.*—Fine, fibrous, free branching.

*Color.*—RHS N155B.

Foliage:

*Arrangement.*—Single and opposite, decussate on upright directed stems.

*Peduncle diameter.*—1.5-1.0 cm.

*Texture.*—Rough, densely covered with short glandular hair; hirtellous.

Inflorescence:

*Type.*—Umbel-like, but actually a spike, umbrella-shaped to roughly semi-spherical.

*Blooming habit.*—Flowers continuously.

*Quantity of inflorescences per plant.*—18-22.

*Lastingness of individual blooms on the plant.*—About 5 days in the greenhouse.

*Fragrance.*—None.

*Inflorescence horizontal diameter.*—3.9-4.8 cm.

*Inflorescence depth (height).*—2-3 cm.

*Quantity of flowers and buds per inflorescence.*—20-35.

Bud (just when starting to show color):

*Color.*—Mostly RHS N155C or some slightly RHS 56C.

*Length.*—2.1-2.6 cm.

*Width.*—Up to 0.6 cm.

*Shape.*—Mainly tube-shaped with a bulbous end.

Floret:

*Form and type.*—Sessile; salverform, composed of 5 partly fused petals with a base of a narrow tube.

*Immature color, upper surface.*—RHS 64C with a flush of RHS 64D at the margins fading slightly inward to RHS 64B.

*Lower surface.*—RHS 155A with RHS 63C.

*Mature color, upper surface.*—RHS 64A on the edge to RHS 64C in the center.

*Immature, leaf color, upper surface.*—RHS 137D.

*Lower surface.*—Between RHS 138A and RHS 138B.

*Mature, leaf color, upper surface.*—RHS 137B.

*Lower surface.*—RHS 138A to RHS 138B but a little more yellowish.

*Length.*—4.0-5.5 cm.

*Width.*—2.2-3.2 cm.

*Shape.*—Ovate.

*Base shape.*—Acute to attenuate.

*Apex shape.*—Acute to obtuse.

*Margin.*—Pinnatifid; entire, with incisions of about 0.9-1.2 cm.

*Texture, upper surface.*—Slightly glossy, with sparse, short hair.

*Lower surface.*—Short, stiff hair mainly along the veins; some glandular hairs.

*Color of veins, upper surface.*—RHS 144A becoming indistinct.

*Color of veins, lower surface.*—RHS 145B.

*Petiole color.*—RHS 145B; with RHS 145C on the under side.

*Length.*—0.1-0.4 cm.

*Diameter.*—0.1-0.2 cm.

*Texture.*—Hirtellous.

Stem:

*Characteristics.*—Side branches develop potentially at every node.

*Color of stem.*—RHS 137B.

*Length of stem.*—Approximately 15-25 cm.

*Diameter.*—0.3 cm.

*Length of internodes.*—Approximately 5-6 cm.

*Texture.*—Rough; densely covered with hair; hirsute.

*Color of peduncle.*—RHS 138A.

*Length of peduncle.*—Most often 6-7 cm.

*Lower surface.*—RHS 155A with RHS 64D around the margins.

*Floret diameter.*—1.8-2.1 cm.

*Floret depth.*—1.8-2.2 cm.

*Length of petals.*—0.6-0.8 cm.

*Width of petals.*—0.6-0.9 cm.

*Petal shape.*—Obcordate.

*Apex shape.*—Emarginate.

*Margin.*—Entire.

*Petal texture, upper surface.*—Smooth and glabrous.

*Lower surface.*—Smooth and glabrous.

*Corolla tube length.*—1.8-2.2 cm.

*Corolla tube color inside.*—RHS 150D.

*Tube color outside.*—RHS 150D or sometimes RHS 156D.

*Corolla texture, inside.*—Glabrous.

*Outside.*—Glabrous basally; glandular hairs at the flare.

Calyx:

*Type.*—Five sepals whose margins are fused to each other along their length, with a transparent membrane of less than 0.1 cm in width and with one smaller sepal attached to the base of the calyx.

*Color of sepals.*—RHS 143B to RHS 143C.

*Length of sepals.*—1.0-1.2 cm.

*Width of sepals.*—0.2-0.3 cm.

*Sepal shape.*—Linear.

*Apex shape.*—Acute.

*Margins.*—Entire.

*Texture.*—Densely covered with short hair.

Reproductive organs:

*Pistil.*—1.

*Length.*—1.4-2.0 cm.

*Style color.*—RHS 144B.

*Style length.*—1.3-1.8 cm.

*Stigma color.*—RHS 143B.

*Stamens.*—Anthers and filaments fused to upper half of corolla tube; four anthers with two pollen sacs per anther.

*Color of filaments.*—RHS 150D to RHD 155B.

*Length filaments.*—0.1 cm.

*Anther color.*—RHS N144B.

*Length of anthers.*—0.1-0.15 cm.

*Color of pollen.*—RHS 1B.

*Pollen amount.*—Moderate.

*Fertility/seed set.*—Has not been observed on this hybrid.

Disease/pest resistance: Disease/pest resistance has not been observed on this hybrid.

What is claimed is:

1. A new and distinct variety of *Verbena* plant named 'Plufrena' substantially as illustrated and described herein.

* * * * *

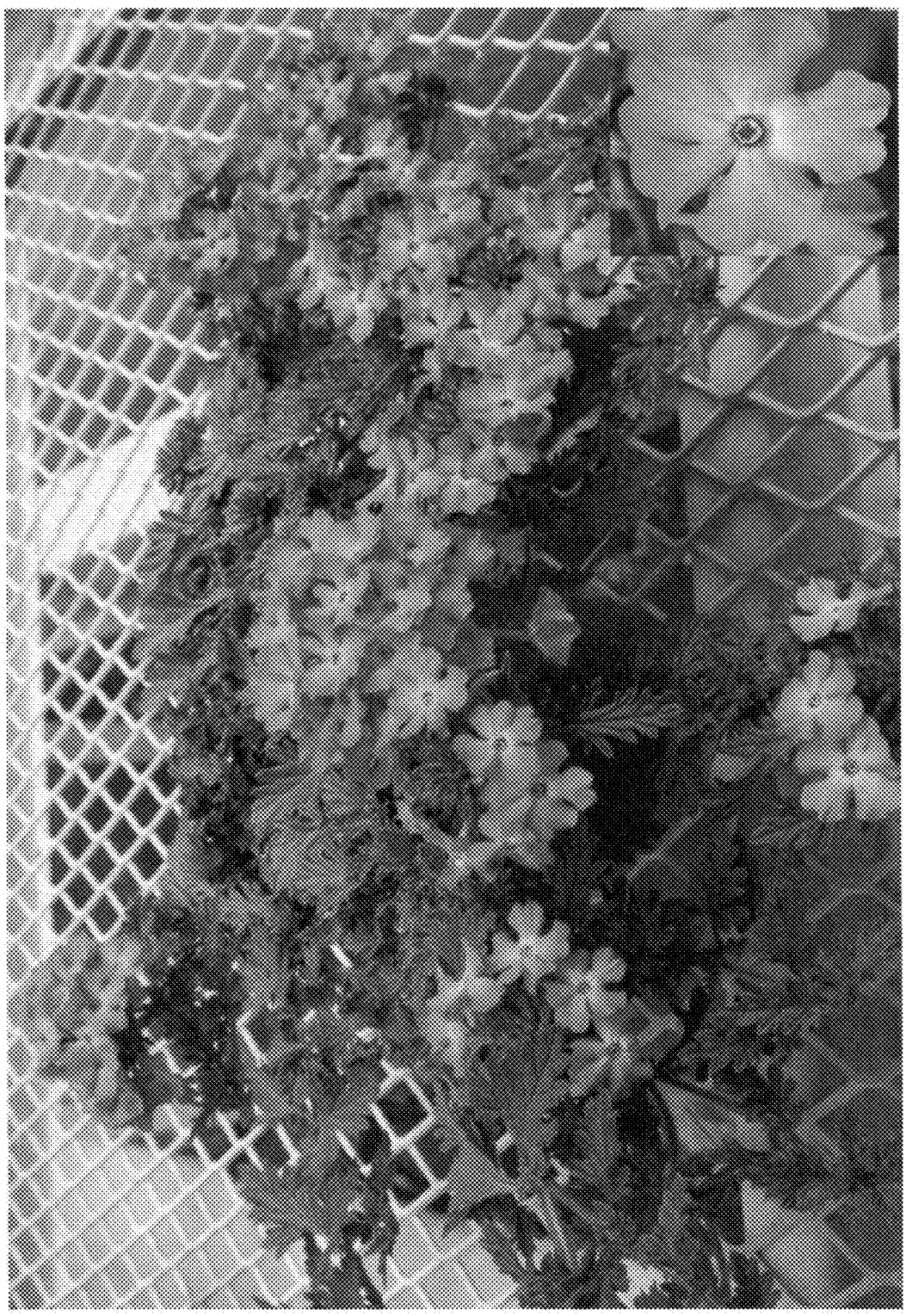

UNITED STATES PATENT AND TRADEMARK OFFICE

CERTIFICATE OF CORRECTION

PATENT NO. : PP22,484 P2
APPLICATION NO. : 12/924085
DATED : February 7, 2012
INVENTOR(S) : Stemkens It is certified that error appears in the above-identified patent and that said Letters Patent is hereby corrected as shown below:

In column 3, under "Foliage:", lines 25-27, should be moved under "Stem:" at column 4, line 23.

Thus, the "Stem:" section at column 4, beginning at line 12 should read as follows:
Stem:
Characteristics: Side branches develop potentially at every node
Color of stem: RHS 137B
Length of stem: Approximately 15-25 cm
Diameter: 0.3 cm
Length of internodes: Approximately 5-6 cm
Texture: Rough; densely covered with hair; hirsute
Color of peduncle: RHS 138A
Length of peduncle: Most often 6-7 cm
Peduncle diameter: 1.5-2.0 cm
Texture: Rough, densely covered with short glandular hair; hirtellous In columns 3 and 4, under "Floret:", line 53 in column 3 through line 11 in column 4, should be moved under "Foliage" at column 3, line 24.

Thus, the "Foliage:" section at column 3, beginning at line 22 should read as follows:
Foliage:
Arrangement: Single and opposite; decussate on upright directed stems
Immature, leaf color, upper surface: RHS 137D
Lower surface: Between RHS 138A and RHS 138B
Mature, leaf color, upper surface: RHS 137B
Lower surface: RHS 138A to RHS 138B but a little more yellowish
Length: 4.0-5.5 cm
Width: 2.2-3.2 cm
Shape: Ovate
Base shape: Acute to attenuate Signed and Sealed this
Twenty-seventh Day of March, 2012

David J. Kappos

David J. Kappos
*Director of the United States Patent and Trademark Office*

Apex shape: Acute to obtuse
Margin: Pinnatifid; entire, with incisions of about 0.9-1.2 cm
Texture, upper surface: Slightly glossy, with sparse, short hair
Lower surface: Short, stiff hair mainly along the veins; some glandular hairs
Color of veins, upper surface: RHS 144A becoming indistinct
Color of veins, lower surface: RHS 145B
Petiole color: RHS 145B; with RHS 145C on the under side
Length: 0.1-0.4 cm
Diameter: 0.1-0.2 cm
Texture: Hirtellous In column 4, under "Stem:", lines 23-39, should be moved under "Floret:" at column 3, line 53.

Thus, the "Floret:" section at column 3, beginning at line 44 should read as follows:
Floret:
Form and type: Sessile; salverform, composed of 5 partly fused petals with a base of a narrow tube
Immature color, upper surface: RHS 64C with a flush of RHS 64D at the margins fading slightly inward to RHS 64B
Lower surface: RHS 155A with RHS 63C
Mature color, upper surface: RHS 64A on the edge to RHS 64C in the center
Lower surface: RHS 155A with RHS 64D around the margins
Floret diameter: 1.8-2.1 cm
Floret depth: 1.8-2.2 cm
Length of petals: 0.6-0.8 cm
Width of petals: 0.6-0.9 cm
Petal shape: Obcordate
Apex shape: Emarginate
Margin: Entire
Petal texture, upper surface: Smooth and glabrous
Lower surface: Smooth and glabrous
Corolla tube length: 1.8-2.2 cm
Corolla tube color inside: RHS 150D
Tube color outside: RHS 150D or sometimes RHS 156D
Corolla texture, inside: Glabrous
Outside: Glabrous basally; glandular hairs at the flare